United States Patent [19]

Yoshida et al.

[11] Patent Number: 4,737,297
[45] Date of Patent: Apr. 12, 1988

[54] SYNTHETIC LUBRICATING OILS

[75] Inventors: Toshio Yoshida, Kawasaki; Harumichi Watanabe, Yokohama, both of Japan

[73] Assignee: Nippon Oil Co., Ltd., Tokyo, Japan

[21] Appl. No.: 8,303

[22] Filed: Jan. 29, 1987

Related U.S. Application Data

[63] Continuation-in-part of Ser. No. 744,817, Jun. 13, 1985, abandoned.

[30] Foreign Application Priority Data

Jul. 5, 1984 [JP] Japan .................................. 59-137885
Jul. 5, 1984 [JP] Japan .................................. 59-137887
Nov. 28, 1984 [JP] Japan .................................. 59-249774

[51] Int. Cl.$^4$ .......................................... C10M 105/06
[52] U.S. Cl. .......................................... 252/9; 585/11; 585/26
[58] Field of Search .................. 252/37.5, 37.7, 73; 585/11, 26, 27

[56] References Cited

U.S. PATENT DOCUMENTS 3,678,123  5/1972  Boggs .............................. 260/671 R
4,665,275  5/1987  Yoshida et al. ........................ 585/27

OTHER PUBLICATIONS

Clemmensen Reduction of 2-Acetonaphithone, Eisenbraun et al., Chemical Abstract 76(11):59296y.
Synthesis of Some Tert-alkylnaphthalenes, Rothberg et al., Chemical Abstract 82(11):72654g.

Primary Examiner—Robert Wax
Assistant Examiner—Hoa Van Le
Attorney, Agent, or Firm—Bucknam and Archer

[57] ABSTRACT

A sysnthetic lubricating oil comprising at least one monosubstituted naphthalene derivative such as β-t.-amylinaphthalene, β-(1,1-dimethyldecyl) naphthalene or β-(α,α-dimethylbenzyl) naphthalene.

3 Claims, 2 Drawing Sheets

SYNTHETIC LUBRICATING OILS

This application is a continuation-in-part of U.S. Ser. No. 744,817 filed June 13, 1985 now abandoned.

BACKGROUND OF THE INVENTION

1. Field of the Invention

This invention relates to a novel synthetic lubricating oil and more particularly to a novel synthetic lubricating oil which is excellent particularly in oxidation stability and comprises, as the main component, at least one mono-substituted naphthalene derivative having a specific structure.

2. Prior Art

Lubricating oils are generally required to have a long-term service life. To meet this requirement, there has usually been used a lubricating oil prepared by adding, as required, a suitable antioxidant to a highly refined mineral oil. It is difficult, however, to use a mineral oil as a lubricant for a long period of time under severe temperature conditions since the mineral oil has limited oxidation stability. Thus, as lubricating oils having better oxidation stability, there have been developed and widely used ester-type synthetic oils such as diesters and polyol esters, and hydrocarbon-type synthetic oils such as poly-α-olefins and alkylbenzenes.

However, although these known synthetic lubricating oils are appreciated to have higher oxidation stability than mineral oils, they are still not satisfactory in stability to oxidation.

The present inventors made intensive studies in attempts to develop synthetic lubricating oils having further higher oxidation stability and, as the result of their studies, found that lubricating oils comprising, as the main component, at least one monosubstituted naphthalene derivative having a specific structure, have remarkably high oxidation stability as compared with the conventional known synthetic lubricating oils. This invention is based on this finding or discovery.

OBJECT OF THE INVENTION

An object of this invention is to provide synthetic lubricating oils which are excellent particularly in oxidation stability.

This and other objects will be apparent from the following description and drawings.

CONSTRUCTION OF THE INVENTION

The synthetic lubricating oil of this invention consists of, or comprises as the main component, at least one monosubstituted naphthalene derivative represented by the following general formula

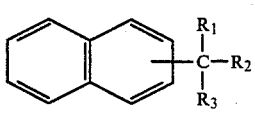

wherein $R_1$, $R_2$ and $R_3$ may be identical with, or different from, each other and are each an alkyl, phenyl or alkylphenyl group having 1 to 21 carbon atoms with the proviso that the total of carbon atoms of $R_1$, $R_2$ and $R_3$ is 4–23.

This invention will be explained hereunder in more detail.

The naphthalene derivatives which makes up, or is comprised as the main component in, the synthetic lubricating oil of this invention is required to be such that:

(1) the hydrocarbon radical is a monosubstituted naphthalene, (2) $R_1$, $R_2$ and $R_3$ of the hydrocarbon radical represented by the general formula

may be identical with, or different from, each other and are each an alkyl, phenyl or alkylphenyl group having 1 to 21 carbon atoms with the proviso that the total of carbon atoms of $R_1$, $R_2$ and $R_3$ is 4 to 23, and (3) the hydrocarbon radical is a tertiary one, i.e., it is attached directly to the naphthalene ring via a tertiary carbon atom. The above three requirements must be met for the purpose of this invention. Naphthalene derivatives which fail to meet even one of said three requirements are undesirable since they are inferior to those used in this invention in the respects of oxidation stability and other physical properties necessary for lubricating oils.

The monosubstituted naphthalene derivative used in this invention may be an α-monosubstituted naphthalene derivative represented by the general formula

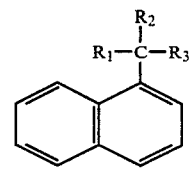

wherein $R_1$, $R_2$ and $R_3$ are as previously defined, or a β-monosubstituted naphthalene derivative represented by the general formula

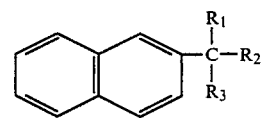

wherein $R_1$, $R_2$ and $R_3$ are as defined above. Of these two types of the derivatives, the β-monosubstituted naphthalene derivative is preferably used since it is easily available and stable as a chemical compound.

Further, $R_1$, $R_2$ and $R_3$ in the hydrocarbon radical represented by the general formula

may be identical with, or different from, each other and are each an alkyl, phenyl or alkylphenyl group having 1 to 21 carbon atoms with the proviso that the total of carbon atoms of $R_1$, $R_2$ and $R_3$ is 4 to 23. In view of the physical properties of monosubstituted naphthalene derivative as a lubricating oil, it is preferable that $R_1$, $R_2$ and $R_3$ be an alkyl, phenyl or alkylphenyl group having 1 to 15 carbon atoms and the total of carbon atoms thereof be 4 to 17. Further, in view of oxidation stability, it is preferred that $R_1$, $R_2$ and $R_3$ are each a straight-chain alkyl group or else two of them are each a straight-chain alkyl group with the other being a phenyl or alkylphenyl group.

The $R_1$, $R_2$ and $R_3$ in the general formula representing the monosubstituted naphthalene derivative used herein, include methyl, ethyl, propyl, butyl, pentyl, hexyl, heptyl, octyl, nonyl, decyl, undecyl, dodecyl, tridecyl, tetradecyl and pentadecyl groups, as well as phenyl, tolyl, xylyl, ethylphenyl, methylethylphenyl, diethylphenyl, propylphenyl, butylphenyl, pentylphenyl, hexylphenyl, heptylphenyl, octylphenyl and nonylphenyl groups. These groups are preferred.

It is particularly preferred that the $R_1$ and $R_2$ are each methyl or ethyl group and the $R_3$ is a straight-chain alkyl, phenyl or an alkylphenyl group having carbon atoms the number of which is such that the total of carbon atoms of the $R_1$, $R_2$ and $R_3$ is 4-17.

The preferable tertiary hydrocarbon radicals of the monosubstituted naphthalene derivatives used herein, the radicals being represented by the general formula

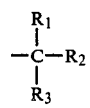

wherein $R_1$, $R_2$ and $R_3$ are as previously defined, include 1,1-dimethylpropyl(t.-amyl), 1-ethyl-1-methylpropyl, 1,1-dimethylbutyl, 1-ethyl-1-methylpropyl, 1,1-dimethylpentyl, 1,1-diethylpropyl, 1,1-dimethylhexyl, 1-ethyl-1-methylpentyl, 1,1-diethylbutyl, 1,1-dimethylheptyl, 1-ethyl-1-methylhexyl, 1,1-diethylpentyl, 1,1-dimethyloctyl, 1-ethyl-1-methylheptyl, 1,1-diethylhexyl, 1,1-dimethylnonyl, 1-ethyl-1-methyloctyl, 1,1-diethylheptyl, 1,1-dimethyldecyl, 1-ethyl-1-methylnonyl, 1,1-diethyloctyl, 1,1-dimethylundecyl, 1-ethyl-1-methyldecyl, 1,1-diethylnonyl, 1,1-dimethyldodecyl, 1-ethyl-1-methylundecyl, 1,1-diethyldecyl, 1,1-dimethyltridecyl, 1-ethyl-1-methyldodecyl, 1,1-diethylundecyl, 1,1-dimethyltetradecyl, 1-ethyl-1-methyltridecyl, 1,1-diethyldodecyl, 1,1-dimethylpentadecyl, 1-ethyl-1-methyltetradecyl, 1,1-diethyltridecyl, 1,1-dimethylhexadecyl, 1-ethyl-1-methylpentadecyl, 1,1-diethyltetradecyl, 1-methyl-1-phenylethyl ($\alpha,\alpha$-dimethylbenzyl), 1-methyl-1-phenylpropyl, 1-ethyl-1-phenylpropyl, 1-methyl-1-tolylethyl, 1-methyl-1-tolylpropyl, 1-ethyl-1-tolylpropyl, 1-methyl-1-xylylethyl, 1-methyl-1-xylylpropyl and 1-ethyl-1-xylylpropyl groups.

The monosubstituted naphthalene derivatives used in this invention may usually be synthesized by a Friedel-Crafts' alkylating reaction. More specifically, a tertiary halogenated hydrocarbon having 4 to 24 carbon atoms as the hydrocarbon source, an alcohol, a branched monoolefin having 4 to 24 carbon atoms and the double bond on the carbon atom of the branched chain, and an $\alpha$-alkylstyrene or the like, are used with naphthalene. Preferably, such a monoolefin and an $\alpha$-alkylstyrene or the like are reacted with naphthalene at a reaction temperature of 0°-250° C. in the presence of a metal halide catalyst such as aluminum chloride, zinc chloride or iron chloride, or an acid catalyst such as sulfuric acid, phosphoric acid, phosphorus pentoxide, fluoric acid, boron fluoride, acid clay or activated clay, to obtain the monosubstituted naphthalene derivative according to this invention. However, there are possibilities that such a Friedel-Crafts' alkylating reaction will disadvantageously cause the transition of carbon cation due to steric hindrance thereby to produce monosubstituted naphthalene derivatives having a secondary hydrocarbon radical in addition to those having a tertiary hydrocarbon radical. Thus, methods for producing monosubstituted naphthalene derivatives having a tertiary hydrocarbon radical only, include a method which comprises acylating naphthalene and then thoroughly methylating the thus acylated naphthalene, and a method which comprises substituting with halogen a hydrogen atom attached to a carbon atom positioned in the branched chain of a monosubstituted naphthalene derivative having a secondary hydrocarbon radial and then reacting the thus substituted product with a trialkyl aluminum.

In a case where there is synthesized a monosubstituted naphthalene derivative having a tertiary hydrocarbon radical by the aforesaid Friedel-Crafts' alkylating reaction, a $\beta$-monosubstituted naphthalene derivative will mainly be produced due to the effect of steric hindrance associated with the hydrogen atom at the 8th position of the naphthalene ring.

The synthetic lubricating oil comprising the aforesaid monosubstituted naphthalene derivative has, per se, particularly excellent oxidation stability in addition to various properties required in ordinary lubricating oils, and it may be incorporated, as required, with usually-used known additives for lubricating oils such as an antioxidant, detergent dispersion, viscosity index improver, pour point depressant, oiliness improver, antiwear agent, extreme pressure agent, anticorrosive agent, metal inactivating agent, antirust agent, antifoaming agent, emulsifier, demulsifier, bactericide, colorant and/or the like. The various additives mentioned above are described in detail in publications such as "Junkatsuyu Gakkai Shi (Journal of Japanese Society of Lubricating Oils)", vol. 15, No. 6 or "Sekiyu Seihin Tenkazai (Additives for Petroleum Products)" edited by Toshio Sakurai and published by Sachi Shobo Book Store.

The known additives may be added in an amount by weight of up to 20%, preferably up to 10%, of the total amount of the monosubstituted naphthalene derivative according to this invention and the additives.

Further, the synthetic lubricating oils of this invention may be incorporated, as required, with mineral oils and/or known lubricating oils in such amounts as not to impair their high oxidation stability. The mineral oils and/or known lubricating oils may be added in an amount by weight of up to 50%, preferably up to 20%, of the total amount of the monosubstituted naphthalene derivative according to this invention and the mineral oils and/or known lubricating oils.

Thus the compositions according to the present invention may be represented as follows:

| Components | Ratio (wt %) |
| --- | --- |
| Monosubstituted naphthalene | 50–100, preferably 80–100 |
| Mineral oil and/or known lubricating | 0–50, preferably 0–20 |
| Additives (total) | 0–20, preferably 0–10 |

The synthetic lubricating oils containing at least one of the monosubstituted naphthalene derivatives according to this invention, can be used as gasoline engine oils, diesel engine oils, turbine oils, gear oils, hydraulic working oils, compressor oils, refrigerator oils, metal working oils, slip guide surface oils, bearing oils and the like.

BRIEF DESCRIPTION OF THE DRAWINGS

In the accompanying drawings.

PREFERRED EMBODIMENTS

Figure 1:
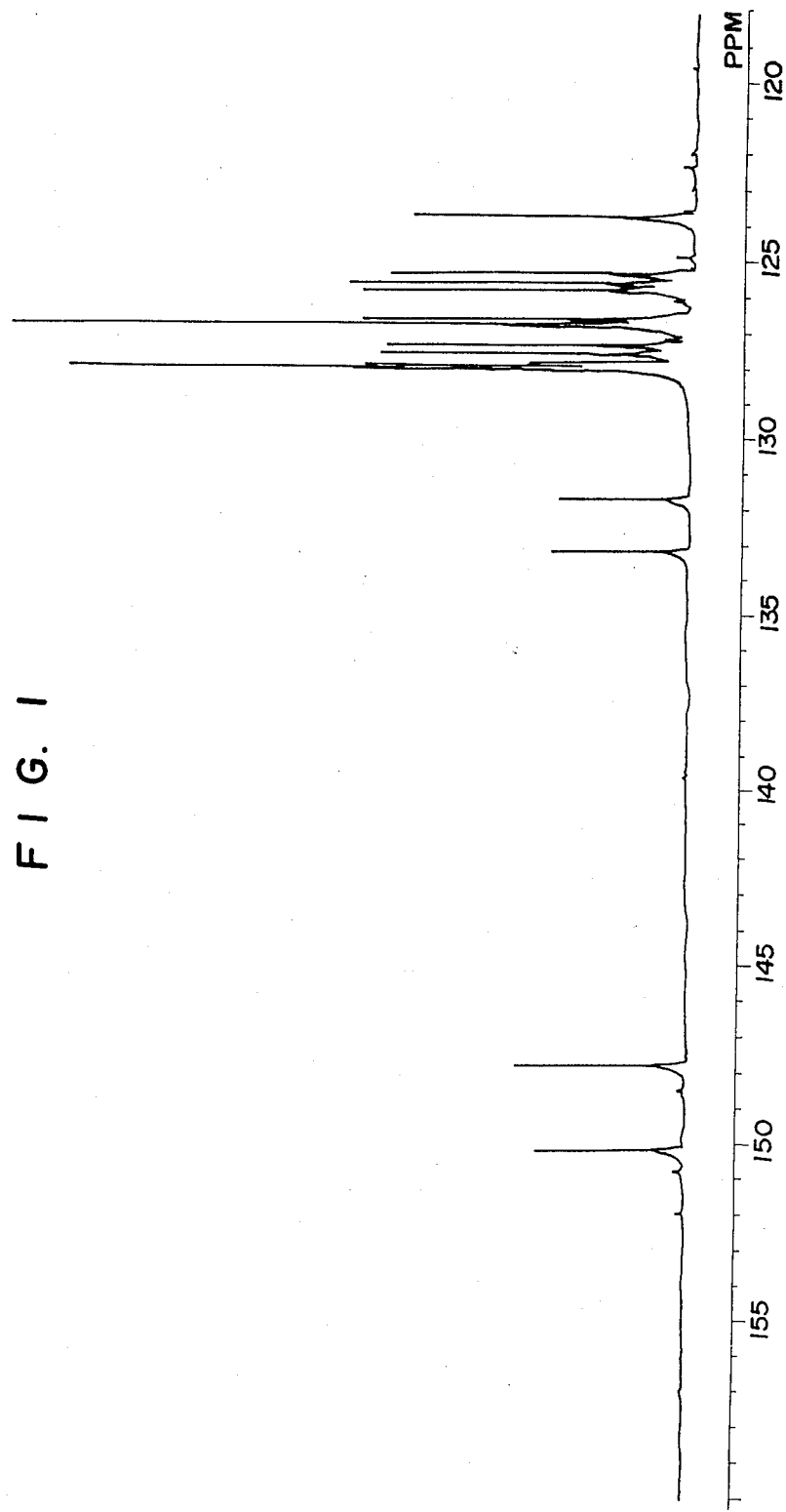
FIG. 1 shows $_{13}$C-NMR spectra of 1,2-($\alpha,\alpha$-dimethylbenzyl)naphthalene which is one of the monosubstituted naphthalene derivatives according to this invention.
Figure 2:
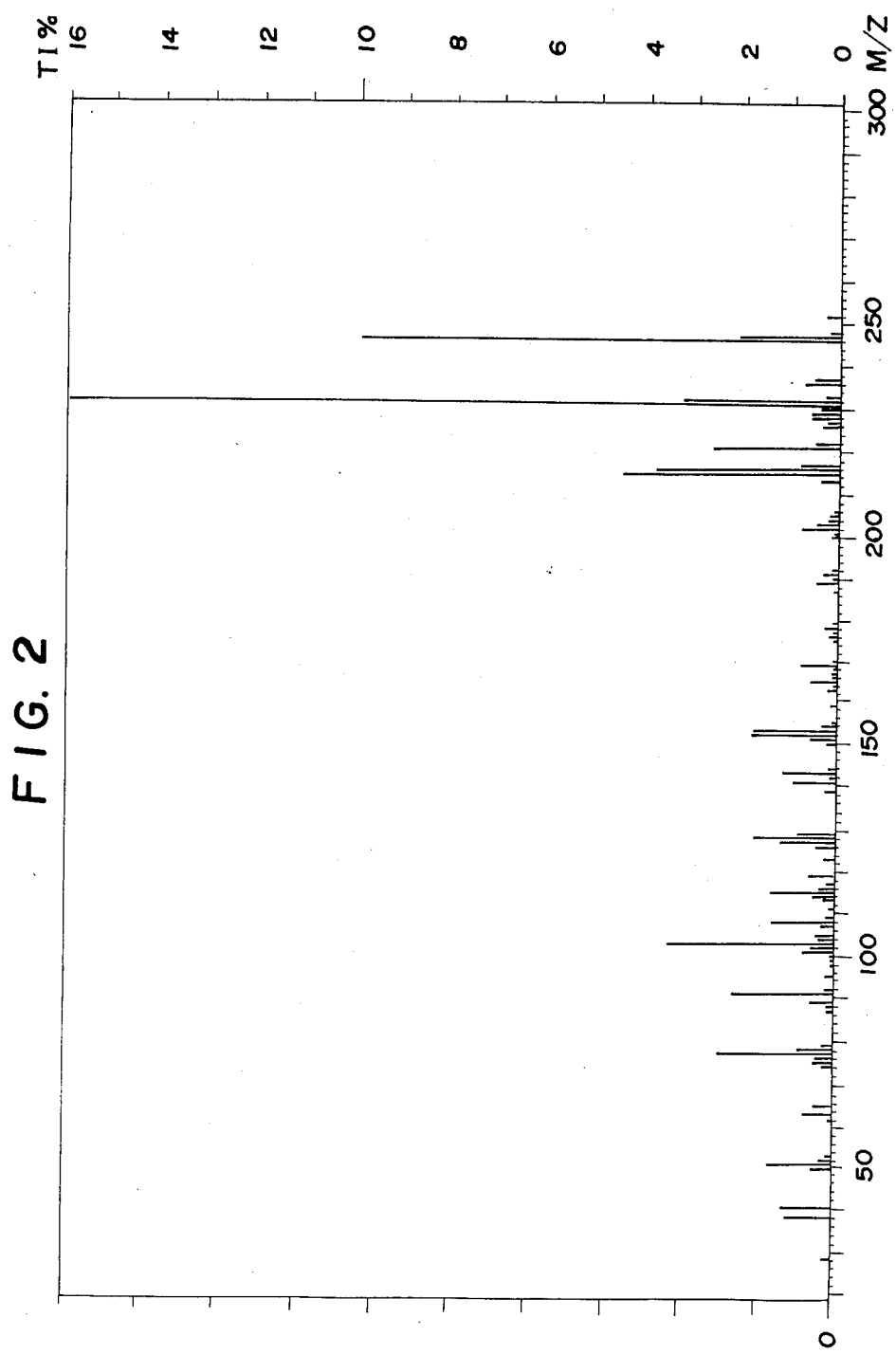
FIG. 2 shows EI mass spectra.

This invention will be better understood by the following Examples and Comparative Examples wherein all parts are by weight unless otherwise specified.

EXAMPLE 1

One thousand (1000) parts of naphthalene were introduced into a four-necked flask, heated to 150° C. under agitation in a nitrogen atmosphere, incorporated with 100 parts of activated clay baked at 220° C. and then heated to 200° C., after which the whole was incorporated dropwise in small portions with 300 parts by 2-methyl-2-butene over a time period of 4 hours and kept at 200° C. under agitation for one hour to react the naphthalene with 2-methyl-2-butene.

After completion of the reaction, the reaction mixture was cooled to 100° C. and filtered to obtain a filtrate which was then distilled under reduced pressure (1 mmHg) to obtain $\beta$-t.-amylnaphthalene as the end product. The yield of this product was 76%, based on the 2-methyl-2-butene. The thus obtained $\beta$-t.-amylnaphthalene had the following properties:

Viscosity:
 5.2 cSt at 40° C.
 1.5 cSt at 100° C.
Pour point: < −45° C.
Boiling point: 128° C. at 2.0 mmHg

EXAMPLE 2

Seven hundred (700) parts of naphthalene were introduced into a four-necked flask, heated to 150° C. under agitation in a nitrogen atmosphere and incorporated with 100 parts of activated clay baked at 220° C., after which the resulting mixture was incorporated dropwise in small portions with 500 parts of 2-methyl-1-nonene over a period of time of 4 hours and then kept at 200° C. under agitation for one hour to react the naphthalene with the 2-methyl-1-nonene.

After completion of the reaction, the reaction mixture was cooled to 100° C. and filtered to obtain a filtrate which was then distilled under reduced pressure (1 mmHg) to obtain $\beta$-(1,1-dimethyloctyl)naphthalene. The thus obtained naphthalene derivative had the following properties:

Viscosity: 14.86 cSt at 40° C.
Pour point: 31 45° C. or lower
Boiling point: 165° C./1 mmHg

EXAMPLE 3

The procedure of Example 2 was followed except that 2-methyl-1-heptene was substituted for the 2-methyl-1-nonene, thereby to obtain $\beta$-(1,1-dimethylhexyl)-naphthalene having the following properties:

Viscosity: 10.65 cSt at 40° C.
Pour point: −45° C. or lower
Boiling point: 144° C./1 mmHg

EXAMPLE 4

The procedure of Example 2 was followed except that 2-methyl-1-undecene was substituted for the 2-methyl-1-nonene, thereby to obtain $\beta$-(1,1-dimethyldecyl)naphthalene the properties of which are as indicated below.

Viscosity: 17.63 cSt at 40° C.
Pour point: −45° C. or lower
Boiling point: 185° C./1 mmHg

EXAMPLE 5

Naphthalene (457 parts) was charged into a four-necked flask, heated to 150° C. under agitation in a nitrogen atmosphere, incorporated with 80 parts of activated clay baked at 220° C. and heated to 200° C., after which the resulting mixture was incorporated dropwise in small portions with 307 parts of $\alpha$-methylstyrene over a period of time of 4 hours and then kept at 200° C. under agitation for one hour to react the naphthalene with the $\alpha$-methylstyrene.

After the end of the reaction, the reaction mixture was cooled to 100° C. and filtered to obtain a filtrate which was distilled under reduced pressure (1 mmHg) to obtain $\beta$-($\alpha,\alpha$-dimethylbenzyl)naphthalene in a yield of 82%, based on the $\alpha$-methylstyrene. The thus obtained $\beta$-($\alpha,\alpha$-dimethylbenzyl)naphthalene had the following properties:

Viscosity:
 65.9 cSt at 40° C.
 4.4 cSt at 100° C.
Pour point: −5° C.
Boiling point: 142° C. at 1.0 mmHg
Index of refraction: 1.622 at 20° C.

COMPARATIVE EXAMPLES 1-4

A decene-1 oligomer having an average molecular weight of about 500 (Comparative Example 1), dioctyl sebacate (Comparative Example 2), pentaerithritol tetracapriate (Comparative Example 3) and diisopropylnaphthalene (Comparative Example 4), were used for comparison with the monosubstituted naphthalene derivatives of this invention (Examples 1-5).

EXPERIMENTS (OXIDATION TESTS ON THE END COMPOUNDS OF EXAMPLES 1-5 AND COMPARATIVE EXAMPLES 1-4)

The end products of Examples 1-5 and Comparative Examples 1-4 were subjected to high-temperature oxidation tests using a test equipment prescribed in IP-280. The test conditions were as follows:

Test temperature: 170° C.
Flow of oxygen: 3 l/hr
Catalyst: Copper wire 1 mm$\phi \times$80 cm.

The evaluation for oxidation stability was made by measuring how long each of the test compounds took to reach 1.0 mg KOH/g in acid value. The time so taken was assumed to be a service life at oxidation test. The results are as indicated in Table 1.

TABLE 1

| | Test Compound | Service life at oxidation test (hr) |
|---|---|---|
| Example 1 | $\beta$-t.-amylnaphthalene | 400.0 |
| Example 2 | $\beta$-(1,1-dimethyloctyl) naphthalene | 250.0 |
| Example 3 | $\beta$-(1,1-dimethylhexyl) naphthalene | 250.0 |

TABLE 1-continued

|  | Test Compound | Service life at oxidation test (hr) |
| --- | --- | --- |
| Example 4 | β-(1,1-dimethyldecyl) naphthalene | 230.0 |
| Example 5 | β-(α,α-dimethylbenzyl) naphthalene | 700.0 |
| Comp. Example 1 | Decene-1 oligomer (Av. Mol. Wt., about 500) | 2.8 |
| Comp. Example 2 | Dioctyl sebacate | 2.8 |
| Comp. Example 3 | Pentaerithritol tetracapriate | 3.0 |
| Comp. Example 4 | Diisopropylnaphthalene | 2.0 |

It is apparent from the results (service lives at oxidation test) that the synthetic lubricating oils comprising the monosubstituted naphthalene derivative of this invention have very high oxidation stability, whereas the poly-α-olefin, diester, polyester, alkylnaphthalene and the like which have heretofore been considered to have excellent oxidation stability, are very inferior in said service life to the compounds of this invention.

As is seen from the foregoing, the synthetic lubricating oils comprising at least one monosubstituted naphthalene derivative of this invention have such high oxidation stability that conventional known synthetic lubricating oils would not be able to attain.

What is claimed is:

1. A method of lubrication which consists of applying to the structure to be lubricated a synthetic oil composition which comprises as the main component at least one monosubstituted naphthalene derivative represented by the general formula

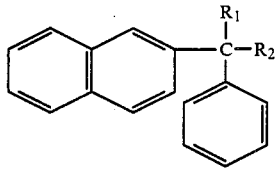

wherein $R_1$ and $R_2$ are the same or different and each is methyl or ethyl.

2. The method according to claim 1, wherein the monosubstituted naphthalene derivative is β-monosubstituted naphthalene derivative of formula

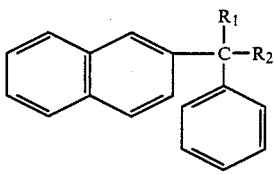

3. The method according to claim 1, wherein the monosubstituted naphthalene derivative is β-αα-dimethylbenzyl)naphthalene.

* * * * *